United States Patent [19]

Tauber et al.

[11] Patent Number: 4,927,518
[45] Date of Patent: May 22, 1990

[54] REFERENCE ELECTRODE HAVING IMMOBILIZED ELECTROLYTE

[75] Inventors: Gunter Tauber, Kriftel; Andrea Dornauf, Kelkheim, both of Fed. Rep. of Germany

[73] Assignee: Schott Glaswerke, Fed. Rep. of Germany

[21] Appl. No.: 359,972

[22] Filed: Jun. 1, 1989

[30] Foreign Application Priority Data

Jun. 3, 1988 [DE] Fed. Rep. of Germany ....... 3818846

[51] Int. Cl.$^5$ .............................................. G01N 27/30
[52] U.S. Cl. ..................................... 204/421; 204/435
[58] Field of Search ....................... 204/435, 421, 414

[56] References Cited

U.S. PATENT DOCUMENTS 3,192,144  6/1965  Heuze .................................. 204/435
4,235,688  11/1980  Sudrabin et al. .................... 204/435

FOREIGN PATENT DOCUMENTS 3228647  2/1984  Fed. Rep. of Germany .
3405431  11/1987  Fed. Rep. of Germany .

*Primary Examiner*—G. L. Kaplan
*Attorney, Agent, or Firm*—Fuller, Ryan & Hohenfeldt

[57] ABSTRACT

A reference electrode which makes use of an electrolyte which is immobilized by mixing it with an hydraulically setting inorganic material. The hydraulically setting materials that can be used are plaster of Paris, cement or mixtures thereof which can be mixed with aggregates commonly used in cements. The electrodes are characterized by ease of manufacture and stability with regard to high pressure and temperature changes.

9 Claims, 1 Drawing Sheet

REFERENCE ELECTRODE HAVING IMMOBILIZED ELECTROLYTE

BACKGROUND OF THE INVENTION

The invention disclosed herein pertains to a reference electrode having an immobilized electrolyte which makes electrical contact with a reference element and can be brought into contact with a test solution which is to be measured either directly or through a bridging electrolyte. The reference electrolyte and, if present, the bridging electrolyte is immobilized by means of an hydraulically setting inorganic cementitious material, that is, an aqueous solution of the electrolyte is mixed in the material before it sets.

It is known to reduce maintenance costs and improve operation of reference electrodes by immobilizing the electrolyte. To achieve immobilization, the reference electrolyte is generally a sodium or potassium chloride solution densified with a natural or synthetic polymer to obtain various degrees of stiffness. German application DE-PS 9 39 597 describes a low maintenance reference electrode which contains a potassium chloride electrolyte gel. The gel contains air bubbles which are intentionally included in order to allow compensation for the great differences in thermal expansion between the gel and the material composing the electrode body due to temperature variations whereby bursting of the electrode body is avoided. When there is expansion and compression of air bubbles at a constant temperature but with changing pressure, the measuring solution can be forced through the diaphragm of the electrode into the reference electrolytes and, especially in the presence of substances toxic to the electrodes, undesirable alteration of the reference potential may occur.

In German Patents DE OS 323 28 647 and DE PS 34 05 431 reference electrodes are described which are filled with gelled reference electrolytes in which there are no air bubbles.

These reference electrodes are suited for use with changing pressures but they are not well suited for use under changing temperature conditions. In these electrodes, bursting of the electrode body is avoided by providing the body with an opening through which, when a positive temperature is developed, the gelled electrode can escape to relieve the pressure. But if the temperature is lowered, the gel again contracts so an undesirable pumping effect occurs which can extend to the electrode body by means of a measuring solution and sooner or later leads to a reference electrode that will not operate.

SUMMARY OF THE INVENTION

An object of the invention is to provide a reference electrode which is simple in construction and economical to produce and is also highly stable under changing temperature and pressure conditions.

In contrast to known electrodes, the electrolyte is not immobilized by an organic polymer or a high viscosity gel, but rather by means of an hydraulically setting inorganic material. Hydraulically setting inorganic materials, which are also described as hydraulic cementing agents, are those which become hard as stone by hydrolysis in air and even under water. Hydraulically setting media are readily available commercially. These are primarily cements based on calcium silicates or aluminates or materials composed of gypsum. After hardening, the cements are completely stable in water. Gypsum materials, however, being composed of calcium sulphate, are slightly soluble in water and not completely resistant to water, but in general still provide quite satisfactory results for the required purpose.

Besides the mentioned cements that are based on calcium silicates or aluminates or gypsum, other hydraulically setting media are also suitable. Examples are Suevite trass cement, high alumina cement, quick-setting cement (controlled setting cement), expansion cement, sulphate blast furnace cement, Roman cement and the like. The composition and production of the cement and plaster of Paris are known to specialists and are described, for example, under the reference "Cement" in Neumiller, Otto-Albrect: Rompps Chenie Lexiocon, French Publishing House, Stuttgart, 7th Edition, 1977 or in Ulmanns Encyclopedia of Industrial Chemistry, VCH Weinheim, New York, N.Y. Vol. A5, 5th Edition, 1986, pp. 489–544.

Any hydraulically setting media which is selected must be suited to the desired use, that is, the media should give off no interfering ions to the solution which is to be measured or enter into undesirable reactions with the solution which is to be measured. Alkali-free cement and plaster of Paris which are as neutral as possible are therefore preferred.

Hydraulically setting materials, in particular materials that have a cement base, can, in a manner known in and of itself, contain up to 75% inert filler (aggregate) by weight. Twenty-five to 50% of filler by weight is preferred. Reactive rock dust or fine grain sand can be used as a filler material, while quartz or pozzolan are particularly suitable. Pozzolan is a porous variety of volcanic tuff or ash used in making hydraulic cement. It is sometimes spelled pozzolana, pozzuolana, and puzzolana. The porosity of the set or cured hydraulic material and its shrinkage behavior are influenced by the addition of filler materials and their fines. The finer the filler material particles, the lower the porosity. The higher the filler particle content, the smaller will be the changes in length, that is stretching or shrinking, during setting.

To incur mechanical stability, the cementitious material can advantageously also contain organic or inorganic reinforcing fibers which also function as filler material. Glass and cellulose reinforcing and filling fibers are preferred in quantities of 5% to 25% by weight although quantities up to 30% by weight are acceptable. Fibers having a length of about 5 mm to 30 mm are desirable. The hydraulically setting materials can contain the usual additives such as a plasticizer medium, accelerating agent or retarder and the like to the extent that they do not negatively affect the overall usage.

The setting media and the aggregate media are advantageously selected such that the thermoexpansion of the cured material used for the glass or plastic casing material is highly suited to the reference electrode which is possible with a minimum amount of investigation. Building supply stores and hardware stores offer numerous ready-to-use, partially fiber containing mixtures composed of cementing agents. Aggregates and additives in the form of ready-to-use mortar, bonding materials, plaster and other usable materials are readily available. These materials are, in general, suited in their existing form for immobilizing electrolytes.

During production of the unitary reference electrode, the hydraulically setting material has an aqueous solution or gel electrolyte of sodium or potassium chloride molded with the material into the case of the reference electrode in a paste or pliable form. The polarity of the solidified hydraulic material and the conductivity of the immobilized electrolyte distributed in it can, aside from the already mentioned admixed material, also be influenced within certain limits by the quantity of electrolyte used in the hydraulically setting paste. Large quantities of electrolytes result in greater porosity and larger pores. The electrolyte quantity used for forming a paste of the hydraulically setting material has a lower limit, defined by minimum water quantity needed for setting, and an upper limit results from the requirement that the electrolyte be immobilized. In any case, after the curing process is complete, a homogeneous solid mass should be formed. After being cured, the unitary reference electrode rod is ready for use. It is also possible to initially place a suitable bridging electrode in the paste or fluidd form in the casing and then connect it, that is, normally to layer it, with a second paste electrolyte in which the electrode system is arranged.

Illustrative embodiments of the new electrode will now be described in greater detail in reference to the accompanying drawings.

DESCRIPTION OF A PREFERRED EMBODIMENT

Figure 1:
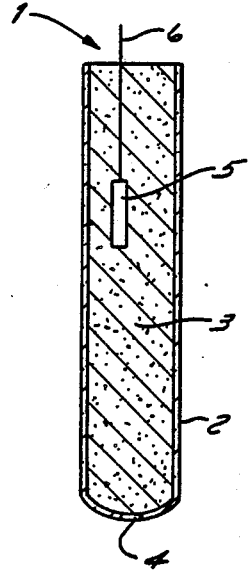
FIG. 1 is a longitudinal section of one embodiment of a new type electrode.

FIG. 1 shows a measuring probe in the form of a reference electrode having a casing 2 composed of electrically insulating material such as glass or plastic. Casing 2 contains the reference electrolyte 3 which can be brought into contact with a solution which is to be measured by means of at least one hole 4 through the casing. The reference electrolyte 3 is immobilized by means of an hydraulically setting material such as those which have been suggested above. The material having the previously described properties which make it suitable as a reference electrode has been molded in casing 2 and is transformed into a stone-like mass. The electrode 5 which may be Ag/AgCl electrode has a known potential and is arranged in the solid state reference electrolyte 3 such that the electrical potential of electrode 5 can be sensed on the fine conductive wire 6 which is commonly platinum. The electrode 5 with wire 6 fastened to it is simply immersed in the pasty settable hydraulic material during molding. After the hydraulic material sets, the electrode is immobilized and fixed in the reference electrolyte 3 in which the electrode is insoluble. The opening 4 at the tip of the electrode body can also be provided with a permselective membrane, not shown.

Figure 2:
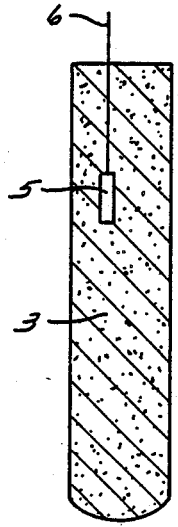
FIG. 2 is a longitudinal section of another embodiment of the new reference electrode.

FIG. 2 shows an alternative embodiment of the new electrode in which the parts that correspond with the parts in FIG. 1 are given the same reference numeral. The only difference between the FIG. 1 and FIG. 2 embodiments is that the casing 2 is omitted from the FIG. 2 embodiment. The hydraulically setting electrolyte holding material 3 is rigid and self-supporting without a casing. Making the FIG. 2 measuring probe can be carried out by forming a paste or pliable mass of one of the previously mentioned hydraulically setting materials and this mass is put into a mold in which electrode 5 and conductor 6 are suspended. After setting, the unitary electrode rod is removed from the mold. In this case the reference electrode body 3, if a particular application requires it, can be coated on its surface with an impenetrable electrically insulating layer, not shown, that results from dipping it into an enamel bath. In general, however, it is more advantageous to work with a casing 2 composed of an inexpensive material.

Figure 3:
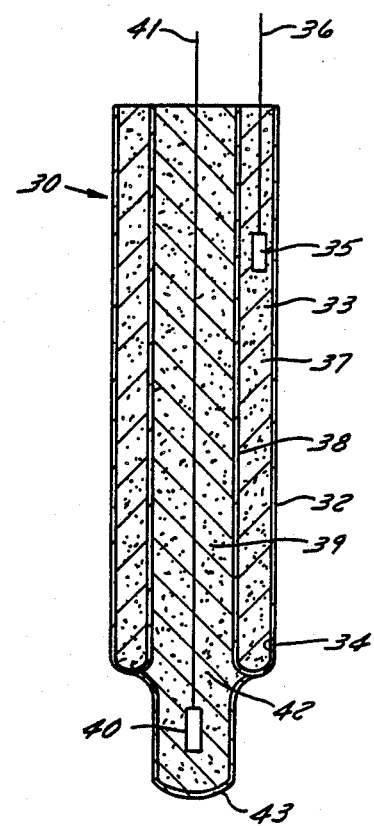
FIG. 3 is a longitudinal section through a unitary composite electrode.

FIG. 3 schematically illustrates a unitary rod like measuring electrode 30 including a casing comprised of an outer wall 32 and inner wall 38 which are composed of electrically insulating material such as glass. The casing contains an opening 34 through which the reference electrolyte 33 which is located in the annulus 37 formed by the outer wall 32 and the inner wall 38, can be brought into contact with a solution which has a property that is to be measured. Reference electrolyte 33 is contained in and is immobilized in hydraulically setting material. In the solid state cementitious reference electrolyte 33 there is a reference electrode 35, consisting of silver foil coated with silver chloride. The potential of which is acessible from the outside by means of a fine wire conductor 36 which is preferably platinum. The annulus 37 surrounds an inner volume in which an electrolyte is immobilized by having it intermixed with an hydraulically setting material 42. The potential of silver chloride coated silver electrode 40 is made accessible to the outside by means of a fine wire 41 which is preferably platinum. The inner core which is surrounded by inner wall 38 of the annulus comprises the hydraulically settable material 42 in which a buffered electrolyte is intermixed. In order to permit the exchange of ions between the buffer in solid material 42 and the solution which contains the substance to be measured, the lower part of the inner electrode is provided with an ion sensitive membrane 43 of glass, for example.

EXAMPLE I

An electrolyte consisting of a saturated potassium chloride solution was mixed into a viscous paste with an hydraulically setting material composed of 2 parts by weight of plaster and 1 part by weight of quartz powder, and filled into a glass casing according to FIG. 1, which contains a silver/silver chloride electrode.

EXAMPLE II

Example I was repeated but with an hydraulically setting material composed of 4 parts by weight of Portland cement and 1 part of quartz powder.

EXAMPLE III

Example I was repeated but with an hydraulically setting material composed of 3 parts by weight of cement, 1 part by weight of quartz powder, 1 part by weight of fibers having a length of about 5 mm.

EXAMPLE IV

Example I was repeated but with an hydraulically setting material composed of 12 parts by weight of cement, 7 parts by weight of quartz powder, 1 part by weight of methylcellulose as a plasticizer agent.

The reference electrode produced according to Examples I-IV were tested as follows:

1. Stability Related to the Potential: The potentials of the reference electrodes were measured relative to a commercially available reference electrode of the silver/silver chloride type at 25° C., 50° C. and 90° C. After heating 100 times to 90° C. for an hour and cooling to 25° C., the potentials were measured again and compared with the values prior to temperature manipulations, and the differences were listed in Table I set forth hereafter. The smaller the potential difference, the better the stability of the potential.

2. Structural Stability: The structural stability of the electrolyte was tested after 20 hours of boiling the reference electrode in 0.1N HCl and 0.1N NaOH. In Table I, the remaining part of the electrolytes is indicated as a percentage.

3. Temperature Change Stability: For testing the thermal expansion relative to the glass casing, the entire reference electrodes were alternately dipped into a cold solution at −15° C. and hot glycerin at 130° C. After numerous temperature changes, neither bursting of the electrode casing or burning-off of the solidified electrode from the wall of the electrode casing could be observed. Furthermore, no change appeared after two days' storage at −30° C.

TABLE I

| Example | 1 | 2 | 3 | 4 |
|---|---|---|---|---|
| potential stability | 4 mV | 6 mV | 3 mV | 1 mV |
| structural stability | 85% | >98% | 95% | >98% |
| thermal expansion | ok | glass breakage (between 0° and 100° C. ok) | ok | ok |

The electrodes possess superb long term stability, withstand high pressures of over 10 bar and changing temperatures, and are highly resistant to temperature shocks of −15° C. to 130° C., and conversely.

We claim:

1. A reference electrode comprising:
   a solidified body of hydraulically setting inorganic material into which an electrolyte was mixed before the material set,
   said hydraulically setting materioal is composed of 12 parts by weight of Portland cement, 7 parts by weight of powdered quartz and 1 part by weight of methylcellulose, and
   an electrode element embedded in said body and an electrical conductor connected to said element and extending through the body of the outside thereof.

2. A reference electrode comprising:
   a solidified body of hydraulically setting inorganic material into which an electrolyte was mixed before the material set,
   said solidified body is composed of 4 parts by weight of Portland cement and 1 part by weight of quartz powder, and
   an electrode element embedded in said body and an electrical conductor connected to said element and extending through the body to the outside thereof.

3. A reference electrode comprising:
   a solidified body of hydraulically setting inorganic material into which an electrolyte was mixed before the material set,
   said solidified hydraulically settable material includes fibers for improving strength, said fibers being selected from the group consisting of glass and cellulose fibers, the quantity of fiber being from 5% to 30% by weight of said material and the fibers having lengths of 2 mm to 30 mm, and
   an electrode element embedded in said body and an electrical conductor connected to said element and extending through the body to the outside thereof.

4. The reference electrode according to any one of claims 1, 2 or 3 including a thin shell of insulating material, selected from the group consisting of plastic and glass, covering said body, said insulating material having a hole for communicating the electrode electrically with a solution being tested.

5. A reference electrode comprising:
   a solidified body of hydraulically setting cementitious material including an electrolyte which is mixed in the material before it is set and wherein said cementitious material is based on materials selected from the group consisting of calcium silicates, calcium aluminates, gypsum, high alumina cement, controlled setting cement, Roman cement and sulphate blast furnace cement, plaster and trass cement, said body further including a filler selected from the group consisting of pozzolan, glass and quartz powder,
   an electrode element embedded in said body and an electrical conductor connected to said element and extending through said body to the outside thereof.

6. The reference electrode according to claim 5 wherein said hydraulically setting cementitious material which is selected is said plaster and there are two parts by weight of plaster and one part by weight of said quartz powder.

7. The reference electrode according to claim 5 wherein said solidified body comprises three parts by weight of the cementitious material which is selected, one part by weight of quartz powder and one part by weight of glass fibers.

8. The reference electrode according to any one of claims 5, 6 or 7 including a thin shell of insulating material selected from the group consisting of plastic and glass covering said body, said insulating material shell having a hole for communicating the electrode electrically with a solution being tested.

9. The reference electrode according to any one of claims 5, 6 or 7 wherein said electrolyte is potassium chloride and said electrode element is silver having a silver chloride coating.

* * * * *